(12) United States Patent
Warner et al.

(10) Patent No.: US 7,314,550 B2
(45) Date of Patent: Jan. 1, 2008

(54) ANALYTICAL SEPARATIONS WITH POLYELECTROLYTE LAYERS, MOLECULAR MICELLES, OR ZWITTERIONIC POLYMERS

(75) Inventors: Isiah M. Warner, Baton Rouge, LA (US); Joseph B. Schlenoff, Tallahassee, FL (US); Constantina P. Kapnissi, Nicolia (CY)

(73) Assignees: Board of Supervisors of Louisiana State University And Agricultural and Mechanical College, Baton Rouge, LA (US); Florida State University, Tallahassee, FL (US)

( * ) Notice: Subject to any disclaimer, the term of this patent is extended or adjusted under 35 U.S.C. 154(b) by 292 days.

(21) Appl. No.: 10/283,471

(22) Filed: Oct. 30, 2002

(65) Prior Publication Data

US 2004/0084312 A1    May 6, 2004

(51) Int. Cl.
    *B01D 15/08*    (2006.01)
(52) U.S. Cl. .................. 210/198.2; 210/502.1; 210/635; 210/656; 204/451; 204/455; 204/601; 204/605
(58) Field of Classification Search ............ 210/198.2, 210/635, 656, 659, 502.1; 204/451, 455, 204/601, 605
See application file for complete search history.

(56) References Cited

U.S. PATENT DOCUMENTS

| | | | |
|---|---|---|---|
| 5,770,084 A | 6/1998 | Warner et al. .............. | 210/635 |
| 6,013,738 A | 1/2000 | Daly et al. .................. | 525/426 |
| 6,270,640 B1 | 8/2001 | Warner et al. .............. | 204/451 |
| 6,402,918 B1 | 6/2002 | Schlenoff et al. ........... | 204/601 |
| 2003/0219384 A1* | 11/2003 | Donath et al. .............. | 424/9.6 |
| 2004/0044100 A1 | 3/2004 | Schlenoff et al. ........... | 523/206 |
| 2004/0265603 A1* | 12/2004 | Schlenoff ..................... | 428/461 |

OTHER PUBLICATIONS

Dulay, M. et al., "Photopolymerized sol-gel monoliths for capillary electrochromatography," *Anal. Chem.*, vol. 73, pp. 3921-3926 (2001).

(Continued)

*Primary Examiner*—Ernest G. Therkorn
(74) *Attorney, Agent, or Firm*—John H. Runnels; Bonnie J. Davis

(57) ABSTRACT

Polymeric surfactants (molecular micelles) are disclosed for use in open tubular capillary electrochromatography or in high performance liquid chromatography. For example, fused silica capillaries are coated with thin films of charged polymers in a polyelectrolyte multilayer (PEM). A PEM coating may be formed in situ by alternate rinses with positive and negative polyelectrolytes. At least the innermost of the negatively charged polymer layers is a molecular micelle. Prototype embodiments have successfully separated seven benzodiazepines from one another. The run-to-run, day-to-day, week-to-week and capillary-to-capillary reproducibilities were very good, with relative standard deviation values less than 0.01. The PEM-coated capillary was very robust over at least 200 runs. Stability against high and low pH values was also observed. Using chiral polymerized micelles, chiral separations may be achieved, as was demonstrated with a separation of the enantiomers of 1,1'-binaphthyl-2,2'-dihydrogenphosphate. Alternatively, layers for use in this invention may be formed from zwitterionic polymers in lieu of separate cationic and anionic layers. Zwitterionic polymer layers may be used either with or without molecular micelles.

9 Claims, 14 Drawing Sheets

OTHER PUBLICATIONS

Graul, T. et al., "Capillaries modified by polyelectrolyte multilayers for electrophoretic separations," *Anal. Chem.*, vol. 71, pp. 4007-4013 (1999).

Harrell, C. et al., "Enhanced separation of antidepressant drugs using a polymerized nonionic surfactant as a transient capillary coating," *Electrophoresis*, vol. 19, pp. 712-718 (1998).

Kapnissi, C. et al., Analytical Chem., vol. 74, pp. 2328 ff (2002).

Katayama, H. et al., "Stable capillary coating with successive multiple ionic polymer layers," *Anal. Chem.*, vol. 70, pp. 2254-2260 (1998).

Katayama, H. et al., "Stable cationic capillary coating with successive multiple ionic polymer layers for capillary electrophoresis," *Anal. Chem.*, vol. 70, pp. 5272-5277 (1998).

Laurent, D. et al., Multilayer assemblies of redox polyelectrolytes, *Langmuir*, vol. 13, pp. 1552-1557 (1997).

Matyska, M. et al., "Open tubular capillary electrochromatography using etched fused-silica tubing modified with chemically bonded liquid crystals," *Anal. Chem.*, vol. 71, pp. 5508-5514 (1999).

Schlenoff, J. et al., Charge and mass balance in polyelectrolyte multilayers, *J. Am. Chem. Soc.*, vol. 120, pp. 7626-7634 (1998).

Schlenoff, J. et al., "Sprayed polyelectrolyte multilayers," *Langmuir*, vol. 16, pp. 9968-9969 (2000).

Schlenoff, J. et al., "Kinetics and multilayering in the adsorption of polyelectrolytes to a charged surface," *Ber. Bunsenges. Phys. Chem.*, vol. 100, pp. 943-947 (1996).

Ye, M. et al., "Capillary electrochromatography using a strong cation-exchange column with a dynamically modified cationic surfactant," *Anal. Chem.*, vol. 72, pp. 616-621 (2000).

J. Wang et al., Anal. Chem., vol. 66, pp. 3773-3776 (1994).

\* cited by examiner

ANALYTICAL SEPARATIONS WITH POLYELECTROLYTE LAYERS, MOLECULAR MICELLES, OR ZWITTERIONIC POLYMERS

The development of this invention was partially funded by the Government under grant number NIGMS/NIH -2 RO1 GM39844-11 awarded by the National Institutes of Health; and under grant numbers CHE-9632916 and CHE-0091726 awarded by the National Science Foundation. The Government has certain rights in this invention.

This invention pertains to methods of analytical separation, for example methods of capillary electrophoresis, high performance liquid chromatography, or capillary electrochromatography, in which the inner layer of the capillary or column has been chemically modified with one or more polymeric bilayers. Alternatively, zwitterionic polyelectrolytes may be used to form the bilayers, or the bilayers may be formed on the surface of particles used in a separation column.

Analytical separation columns can be rather expensive. Chiral separation columns can be particularly expensive. In addition, most existing separation columns, whether chiral or achiral, have relatively short lifetimes.

Capillary electrochromatography (CEC) is a hybrid separation technique that combines the selectivity of high performance liquid chromatography (HPLC) with the separation efficiency of capillary electrophoresis (CE). In CEC separations, CE capillaries are typically packed with an HPLC packing, and a voltage is placed across the column to induce electroosmotic flow. CEC separation is based on both the electrophoretic mobility of the solutes (typical of CE), and on the partitioning of solutes between stationary and mobile phases (typical of HPLC). Studies have demonstrated that CEC provides high resolution, short analysis time, low consumption of sample and buffer, and an efficiency that can be five to ten times higher than that of HPLC.

Both packed columns and open-tubular columns have been used in CEC. Typically, a fused-silica capillary having an internal diameter of 50-100 µm is used, packed with a conventional HPLC stationary phase, such as an octadecyl silica (ODS). However, there are several problems that need to be overcome before packed-CEC can become a viable alternative to either CE or HPLC. One of the limitations of conventional CEC is the need to fabricate frits, which are required to hold the packed particles within the column. Stable frits are difficult to prepare, since they typically require fusion of the capillary by heat or other means. Frits may, for example, be formed in situ by sintering the packing material at the ends of the column. In addition, packed capillaries have a tendency to form bubbles in the packing material or at the frit. Such problems often result in an unstable baseline, irreproducible migration times, or even current breakdown. One approach that has been used to avoid such problems has been to pressurize both ends of the column and to degas the solvent thoroughly. Another common problem in conventional CEC techniques is that column packing tends to be more difficult than that for HPLC, due to the narrow inner diameter of the capillary and the small diameter of the particles. An additional limitation of conventional CEC is that it can be difficult to separate basic compounds; silanol groups on the surface of the silica capillary, which are needed to generate an adequate electroosmotic flow (EOF), tend to dissociate under basic conditions.

Open-tubular capillary electrochromatography (OT-CEC) is an alternative approach to conventional packed-CEC. Many of the problems discussed above may be reduced or even eliminated with an OT-CEC format. In open-tubular capillary electrochromatography, a coating is formed on the inner walls of the capillary. The coating replaces the packed particles, and provides both chromatographic separations and reproducible electroosmotic flow. Wall coatings that have been used to modify the capillary have included: (1) dynamically-created coatings formed by adding a cationic or neutral modifier to the electrolyte solution; (2) cationic modifiers physically adsorbed onto the capillary wall; and (3) hydrophilic layers affixed by covalent bonding or cross linking. However, dynamic coatings can present problems when CEC is coupled to a mass spectrometer (CEC/MS). The presence of nonvolatile buffer constituents can interfere with ionization of the analytes. Although physical adsorption is simple and rapid, and has good reproducibility, physically adsorbed modifiers often have a short lifetime and limited pH range. By contrast, some of the layers formed by covalent bonding or cross-linking have a long lifetime, but require a more complicated coating procedure. There is an unfilled need for a coating procedure that is simple, and that forms a durable and stable coating useful in CEC separations, for use either in chiral or achiral separations.

J. Schlenoff et al., "Kinetics and multilayering in the adsorption of polyelectrolytes to a charged surface," *Ber. Bunsenges. Phys. Chem.*, vol. 100, pp. 943-947 (1996) reports a study of the kinetics of poly (styrene sulfonate) adsorbing at a positively-charged surface. At least under certain conditions, adsorption of the polyelectrolyte onto the surface appeared to be thermodynamically irreversible.

D. Laurent et al., "Multilayer assemblies of redox polyelectrolytes, *Langmuir*, vol. 13, pp. 1552-1557 (1997) discloses the preparation of polyelectrolyte multilayers containing redox active units.

J. Schlenoff et al., "Charge and mass balance in polyelectrolyte multilayers, *J. Am. Chem. Soc.*, vol. 120, pp. 7626-7634 (1998) reports an analysis of the ion and polymer content of polyelectrolyte multilayers that were probed by radioanalytical methods. Among other things, it was reported that the multilayers generally contained little or no salt ions, and that excess charge generally resided on the surface.

H. Katayama et al., "Stable cationic capillary coating with successive multiple ionic polymer layers for capillary electrophoresis," *Anal. Chem.*, vol. 70, pp. 5272-5277 (1998); and H. Katayama et al., "Stable capillary coating with successive multiple ionic polymer layers," *Anal. Chem.*, vol. 70, pp. 2254-2260 (1998) disclose a coated capillary prepared by alternately coating cationic and anionic polymer layers on the capillary inner wall, and analytic separations conducted with the coated capillary.

C. Harrell et al., "Enhanced separation of antidepressant drugs using a polymerized nonionic surfactant as a transient capillary coating," *Electrophoresis*, vol. 19, pp. 712-718 (1998) reported a baseline separation of seven tricyclic antidepressants by using a nonionic micelle polymer, poly (n-undecyl-α-D-glucopyranoside) (PUG) in capillary zone electrophoresis.

T. Graul et al., "Capillaries modified by polyelectrolyte multilayers for electrophoretic separations," *Anal. Chem.*, vol. 71, pp. 4007-4013 (1999) discloses the use of fused silica capillaries with polyelectrolyte multilayers in capillary zone electrophoresis. The direction of osmotic electroosmotic flow oscillated as the multilayer surface charge alternated in polarity during buildup. The columns exhibited stable flow rates, and were stable to changes in pH, ionic strength, and hydration/dehydration. Partitioning of neutral solutes using thicker films was reported. See also U.S. Pat. No. 6,402,918.

M. Matyska et al., "Open tubular capillary electrochromatography using etched fused-silica tubing modified with chemically bonded liquid crystals," *Anal. Chem.*, vol. 71, pp. 5508-5514 (1999) discloses attaching two liquid crystal compounds to the inner wall of a fused silica capillary that had been etched with ammonium hydrogen fluoride, and the use of such capillaries to conduct capillary electrochromatographic separations.

M. Ye et al., "Capillary electrochromatography using a strong cation-exchange column with a dynamically modified cationic surfactant," *Anal. Chem.*, vol. 72, pp. 616-621 (2000) discloses the dynamic modification of a strong cation exchange packing with a long-chain quaternary ammonium salt added to the mobile phase, and the use of the resulting hydrophobic layer on the packing as the stationary phase in capillary electrochromatography.

J. Schlenoff et al., "Sprayed polyelectrolyte multilayers," *Langmuir*, vol. 16, pp. 9968-9969 (2000) discloses a method of preparing polyelectrolyte multilayers by sequential spraying of poly (styrene sulfonate) and poly (diallyidimethylammonium) solutions to obtain a thin film over a large area.

M. Dulay et al., "Photopolymerized sol-gel monoliths for capillary electrochromatography," *Anal. Chem.*, vol. 73, pp. 3921-3926 (2001) discloses the preparation of a photopolymerized sol-gel in a capillary column, and its use in separating a mixture of polycyclic aromatic hydrocarbons in capillary electrochromatography.

U.S. Pat. Nos. 5,770,084, 6,013,738; and 6,270,640 disclose polymerized chiral micelles, and their use in performing chiral separations. Various methods for employing the polymerized micelles are mentioned. For example, a paragraph in the '084 patent at col. 13, lines 21-33 states: "In chromatographic applications, polymerized chiral micelles in accordance with the present invention may be present in the mobile phase, or they could instead be incorporated into chiral stationary phases such as gels, wall coatings, and pack capillaries through means known in the art. For example, a gas chromatography capillary column may be packed with silica particles that have been coated with polymerized chiral micelles. Another possibility is the combination of a chiral mobile phase incorporating polymerized chiral micelles in accordance with the present invention, with a different chiral stationary phase. This combination can result in separation efficiencies that are greater than the sum of the parts."

To the inventors' knowledge, there have been no prior reports of the use of a zwitterionic polymer as a dynamic stationary phase in capillary electrochromatography. Zwitterionic polymers such as poly (3-dimethyl methacryloyloxyethyl ammonium propane sulfonate) (PDMAPS) have been used as a stationary phase in ion chromatography for the separation of inorganic anions. The zwitterionic surfactants coco (amidopropyl) hydroxydimethylsulfobetaine (Rewoteric AM CAS U), dodecyldimethyl (3-sulfopropyl) ammonium hydroxide, and hexadecyidimethyl (3-sulfopropyl) ammonium hydroxide have been used as dynamic wall coatings that prevent the adsorption of cationic and anionic proteins and that suppress electroosmotic flow in capillary electrophoresis. Covalently-bonded zwitterionic polymeric stationary phases have also been used for the simultaneous chromatographic separation of inorganic cations and anions; in this approach, the zwitterionic polymer is covalently attached to the separation column.

There remains a continuing need for improved capillaries and columns for chromatographic separations—capillaries and columns that are durable, that are stable, that have high efficiency, that have high resolution, that have unique separation properties, and that are adaptable to perform chiral or achiral separations.

We have discovered an improved coating that is useful in both capillary electrochromatography and in high performance liquid chromatography. One or more cationic polyelectrolyte layers are formed on the inside of the column or capillary, alternating with anionic polyelectrolyte layers. At least the last, or innermost, anionic layer comprises polymeric surfactants (molecular micelles). The polyelectrolyte multilayer (PEM) coating may be formed in situ by alternating rinses of positively and negatively charged polymers: via electrostatic forces, one layer of polymer adds to the existing, oppositely-charged surface, thus reversing the surface charge and priming the film for the addition of another layer. Surprisingly, multilayers formed with molecular micelles were found to have substantially different properties from those formed with linear polyelectrolytes. The novel coatings have several advantages. The coatings are robust and are highly resistant to deterioration from repeated use. Preliminary experiments have found them to be stable for at least 200 runs, perhaps many more. They have novel properties for both chiral and achiral separations. If chiral polymerized micelles are used, then the coatings can be useful in performing chiral separations. Since the polymeric surfactant is coated electrostatically onto the capillary, consumption of the selecting reagent is low—i.e., it does not flush through the capillary with each use. For essentially the same reason, there is less interference in detecting the analyte of interest, which in turn makes the system more amenable to coupling with a mass spectrometer or other detector with which a polymeric surfactant reagent might otherwise interfere.

A significant advantage of the present approach over prior methods of using polymerized micelles in chromatographic applications is that the relatively expensive polymerized micelles may readily be re-used for many separations (hundreds, possibly thousands separations), rather than flushed to waste as in prior methods of micellar electrokinetic chromatography. Relatively inexpensive (perhaps even disposable) separation columns may be made in accordance with the present invention, including columns for chiral separations.

Cationic polymers used in forming the bilayers should have a sufficient charge density to form stable multilayers via electrostatic interaction—the charge density needed may vary as a function of hydrophobicity. Suitable cationic polymers for use in forming the bilayers include, for example, polyelectrolytes with a quaternary ammonium group, such as poly (diallyldimethylammonium chloride) or poly (vinylbenzyltrimethyl ammonium chloride); ionenes; cationic polyacrylamides; poly (acryloxyethyltrimethyl ammonium chloride);poly (methacryloxy(2-hydroxy)propyltrimethyl ammonium chloride); polyelectrolytes with a pyridinium group, such as poly (N-methylvinylpyridine) or other poly (N-alkylvinylpyridines); protonated polyamines such as poly (allylaminehydrochloride) and polyethylenimine; polybrene; and corresponding copolymers.

Suitable anionic polymerized micelles for use in forming the bilayers include poly (sodium N-undecylenic sulfate). For chiral separations, it is preferred that the polymerized micelles also be chiral, for example poly (sodium N-undecylenyl-L-glycinate), poly (sodium N-undecylenyl-L-leucine-L-valinate), poly (sodium N-undecylenyl-L-valinate), poly (sodium N-undecylenyl-L-leucine-L-alininate), and poly (sodium N-undecylenyl-L-glycine-L-leucinate), and other polymerized chiral micelles such as those disclosed, for example, in U.S. Pat. Nos. 5,770,084, 6,013,738; and 6,270,640.

If it is desired to use polyanions other than micelles in some of the "outer" bilayers, suitable polymers include polyelectrolytes containing a sulfonate group, such as poly (styrenesulfonic acid), poly (2-acrylamido-2-methyl-1-propane sulfonic acid), sulfonated poly (ether ether ketone), sulfonated lignin, poly (ethylenesulfonic acid), poly (methacryloxyethylsulfonic acid); polycarboxylates such as poly (acrylic acid), poly (methacrylic acid); sulfates such as carrageenan and dextran sulfate; corresponding salts such as sodium salts of these polyacids; and corresponding copolymers. Anionic polymers used in forming such bilayers should have a sufficient charge density to form stable multilayers via electrostatic interaction—the charge density needed may vary as a function of hydrophobicity.

Without wishing to be bound by this theory, it is believed that polymeric micelles may perform better in separations than linear polyelectrolytes, due to the fact that their more spherical or ellipsoidal shape will tend to have more active sites that do not interact with the surface, and that therefore are more available for interaction with the analyte.

More generally, the invention may be used in other systems containing single or multiple microchannels. There is much current interest in the field of microfluidics, in which fluid is steered in one or more narrow channels or microchannels. A silica capillary, such as typically employed in CEC, is only one example of a microchannel. Some separation techniques employ plates having multiple channels machined into them to perform high throughput separations, for example, separations of biomolecules by electrophoresis. The present multilayer invention may be used in microchannels generally, not just in capillary electrochromatography in silica capillaries.

Alternatively, layers for use in this invention may be formed from zwitterionic polymers in lieu of separate cationic and anionic layers. Zwitterionic polymer layers may be used either with or without molecular micelles.

Figure 1A:
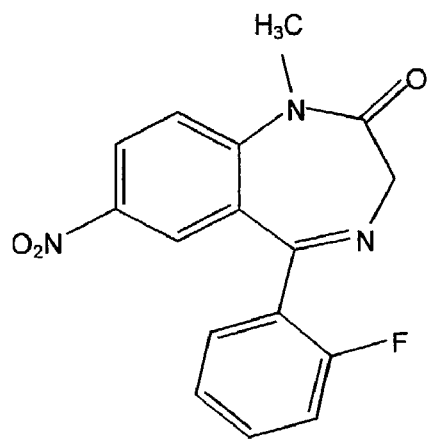
FIGS. 1(a) through (h) depict the structures of the seven benzodiazepine analytes that were used in some of the separations.
Figure 1B:
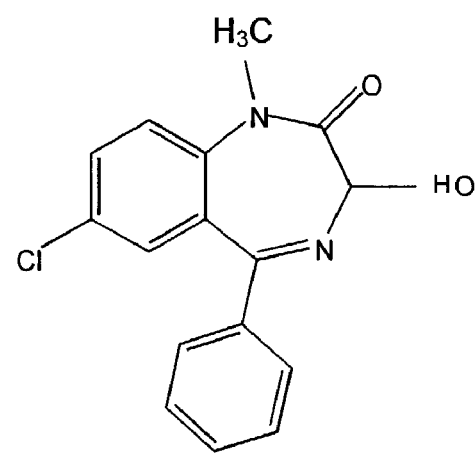
Figure 1C:
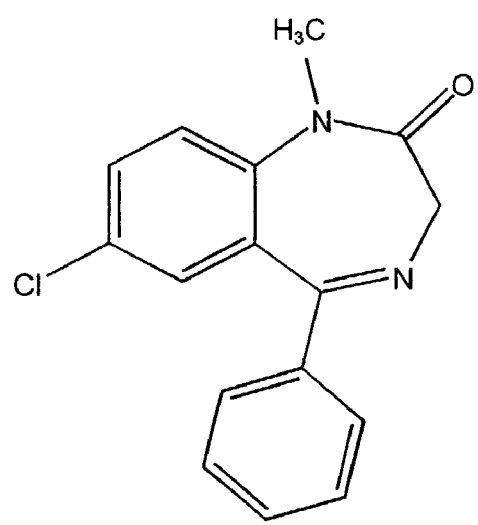
Figure 1D:
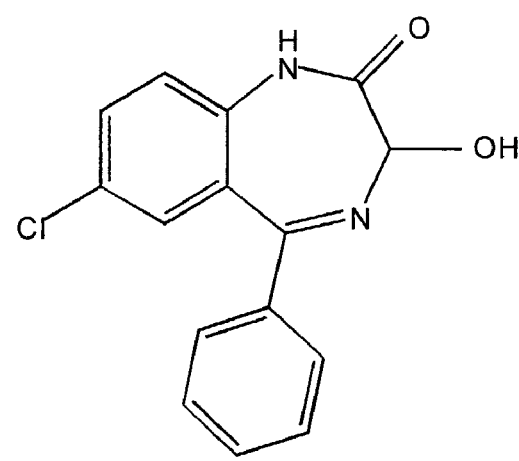

Apparatus and Conditions. Separations were performed on a Beckman P/ACE MDQ capillary electrophoresis system with UV detection (Fullerton, Calif.). A Polymicro Technologies fused-silica capillary, 57 cm (50 cm effective length)×50 µm i.d. (Phoenix, Ariz.) was mounted in a Beckman capillary cartridge. The cartridge temperature was held constant during runs with a liquid coolant. Unless stated otherwise, the temperature was maintained at 25° C. UV detection was conducted at 214 nm. Unless stated otherwise, samples were injected by pressure at 0.1 psi (~700 Pa) for 1 second.

Reagents. Flunitrazepam (FIG. 1(a)), temazepam (FIG. 1(b)), diazepam (FIG. 1(c)), oxazepam (FIG. 1(d)), lorazepam (FIG. 1(e)), clonazepam (FIG. 1(f)), nitrazepam (FIG. 1(g)), and 1,1'-binaphthyl-2,2'-dihydrogenphosphate (BNP) (FIG. 1(g)) were purchased from Sigma Chemical Company (St Louis, Mo.). The structures of these analytes are shown in FIG. 1. Sodium phosphates ($Na_2HPO_4$ and $NaH_2PO_4$), Tris, $Na_2B_4O_7$, hydrochloric acid, and sodium chloride were all obtained from Fisher Scientific (Fair Lawn, NJ). Poly (diallyidimethylammonium chloride), PDADMAC ($M_w$=200,000-350,000) was obtained from Aldrich (Milwaukee, Wis.). Other compounds, including L-glycine, L-leucine, L-valine, undecylenic acid and N-hydroxysuccinimide, were also purchased from Sigma.

Concentrations of the polyelectrolytes may vary within the multilayer. The bilayers may be deposited in the presence of a salt, such as sodium chloride, and may also contain the salt. The bilayers may also comprise a modifier such as an organic solvent, for example ethanol, and may also comprise a weak polyelectrolyte. Such components can help thicken the bilayer, and may also modify its properties.

Sample and Buffer Preparation. Analytical standard benzod iazepine stock solutions were prepared in methanol-water (1:1) at concentrations of about 0.15 mg/mL. BNP stock solution was also prepared in methanol-water (1:1) at a concentration of 0.1 mg/mL. A buffer solution of 50 mM $Na_2HPO_4$ was prepared in 10 mL deionized water. A buffer solution of 100 mM Tris and 10 mM $Na_2B_4O_7$ was prepared in 10 mL deionized water. All solutions were filtered through a polypropylene-nylon filter having a 0.45 µm pore size, and were sonicated for 15 minutes before use.

EXAMPLES 1 and 2

Synthesis of Monomeric and Polymeric Surfactant. The surfactant monomers sodium N-undecylenyl-L-glycinate (mono(L-SUG)), and sodium N-undecylenyl-L-leucine-L-valine (mono(L-SULV))were synthesized from the N-hydroxysuccinimide ester of undecylenic acid as described in J. Wang et al., Anal. Chem., vol. 66, pp. 3773-3776 (1994); and U.S. Pat. Nos. 5,770,084, 6,013,738, and 6,270,640. A 100 mM sodium salt solution of each monomer was then polymerized by $^{60}$Co-γ radiation. After irradiation, the polymers were dialyzed against a 2000 molecular mass cut-off filter, and were then lyophilized to obtain the dry product. The structures of the monomeric and polymeric surfactants are illustrated in FIGS. 2(a)-(d).

EXAMPLE 3

Figure 3:
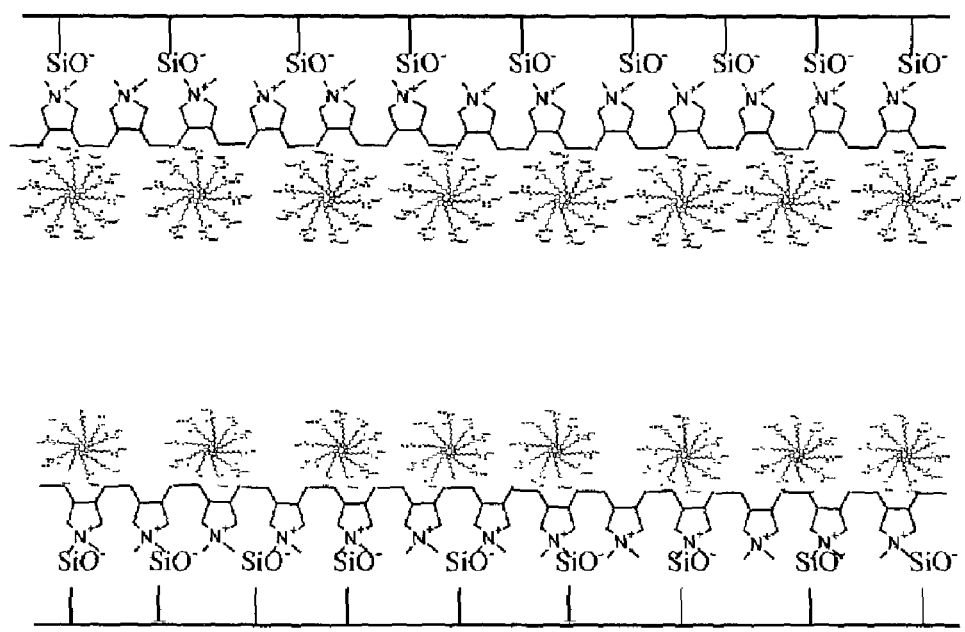
FIG. 3 depicts schematically the structure of one embodiment of a PEM-coated capillary in accordance with the present invention.

Preparing the Polyelectrolyte Multilayer (PEM) Coating. The PEM coating was prepared by depositing the polymer solutions using the "rinse" function on the Beckman CE system. Each polymer deposition solution contained 0.5% (w/v) polymer in 0.2 M aqueous NaCl solution. (Adding NaCl to the polymer solution enhanced the thickness of each polyelectrolyte layer.) The capillary was conditioned before coating with a 5-minute rinse of deionized water to remove contaminants remaining from the capillary drawing process. The column was then conditioned with 1 M NaOH for 60 minutes. Pure deionized water was then flushed through the capillary for 15 additional minutes. The first monolayer of polymer (PDADMAC) was deposited by rinsing the solution of the cationic polymer through the capillary for 20 minutes, followed by a 5-minute water rinse. All subsequent polymer layers were deposited with 5-minute rinses of polymer solution, followed by 5-minute water rinses. (Multiple bilayers can sometimes give more efficient separations than a single bilayer.) A schematic representation of this prototype PEM-coated capillary is shown in FIG. 3. This figure is not intended as an accurate structural representation of the bilayer, but only to represent schematically the order of polymer deposition. As depicted in FIG. 3, the outer layer represents the fused silica capillary, with silanol groups shown on the surface. The next layer is the cationic polymer, PDADMAC. The innermost layer comprises the polymerized micelles. In the benzodiazepine separation examples and reproducibility examples discussed below, the PEM-coated capillary contained ten bilayers. (A "bilayer" pair is a layer of cationic polymer and an adjacent layer of anionic polymer.) Prior to use, the capillaries were flushed with buffer until a stable current was attained. The columns were re-conditioned with buffer for 2 minutes between injections.

EXAMPLE 4

Preparing the Polyelectrolyte Multilayer (PEM) Coating for Chiral Separations. We initially encountered substantial difficulties in obtaining reproducible and robust results for chiral separations using the present invention. In previously work on multilayer polyelectrolyte coatings for capillary electrochromatography, NaCl has typically been added to the polymeric solutions used to lay down the polymeric layers; the NaCl promoted more robust coatings. Surprisingly, we found that the 0.2 M NaCl concentration that we had successfully used in the polymeric solutions for the achiral separation actually caused problems in the reproducibility and the stability of the chiral coatings. Surprisingly, we found that it was beneficial to remove NaCl from the polymeric solutions, and that doing so enhanced the reproducibility and stability of the chiral coatings substantially. We also found that adding an ionic liquid to the polymeric solutions further enhanced the reproducibility and stability of the coatings, and the efficiency of chiral separations using those coatings. The particular ionic liquids that we have used to date are 1-ethyl-3-methyl-1H-imidazolium hexafluorophosphate and 1-butyl-3-methylimidazolium tetrafluoroborate. The chiral coatings were otherwise prepared as generally described above in Example 3, except that the coatings had a single bilayer.

EXAMPLE 5

Measuring Electroosmotic Flow. In CEC, the mobile phase is transferred through the capillary by electroosmotic flow, which in turn is generated by the electrical double layer that forms at the solid-liquid interface between the charged silica surface (or other surface) and the electrolyte solution. Electroosmotic mobility, $\mu_{eo}$, is defined as $$\mu_{eo} = L_d L_t / V t_0$$

where $L_d$ is the distance from injector to detector; $L_t$ is the total capillary length; $t_0$ is the migration time of the electroosmotic flow marker; and V is the applied voltage. If the other parameters are held constant, then $\mu_{eo}$ is inversely proportional to $t_0$. In the results reported here, values for $t_0$ were measured using methanol as a marker, because methanol was not expected to be retained to a significant degree by the OT-CEC column. The electroosmotic mobility ($\mu_{eo}$) and migration time ($t_0$) of methanol were also used to evaluate the stability of the PEM coating.

EXAMPLES 6 THROUGH 8

Durability of PEM Coating. We examined the stability of prototype coatings through the following procedure. A 10-bilayer coating was deposited in a capillary, and nearly 50 separations were performed in a single such coated capillary over a course of five days. Each separation was conducted at applied voltages of 15 to 30 kV at 25° C. The electrolyte was 50 mM $Na_2HPO_4$, and various pH values in the range 9.2-11.0 were used. Following these experiments, the capillary was removed from the instrument, and the tips of the column were placed in water vials for one week. The capillary was then returned to the instrument, and 50 replicate runs were conducted with an applied voltage of 20 kV, a temperature of 25° C., and a 50-mM phosphate buffer (pH 9.2). The capillary was again removed from the instrument, and the tips were placed in water vials for an additional week. The column was then placed returned to the instrument again, and more than 100 additional runs were performed. In this last set of 100 runs, the applied voltage varied from 15 to 30 kV, and the temperature varied from 15° C. to 35° C. Thus the aggregate performance of the PEM-coated capillary was evaluated for over than 200 runs.

EXAMPLES 9 THROUGH 11

Figure 4A:
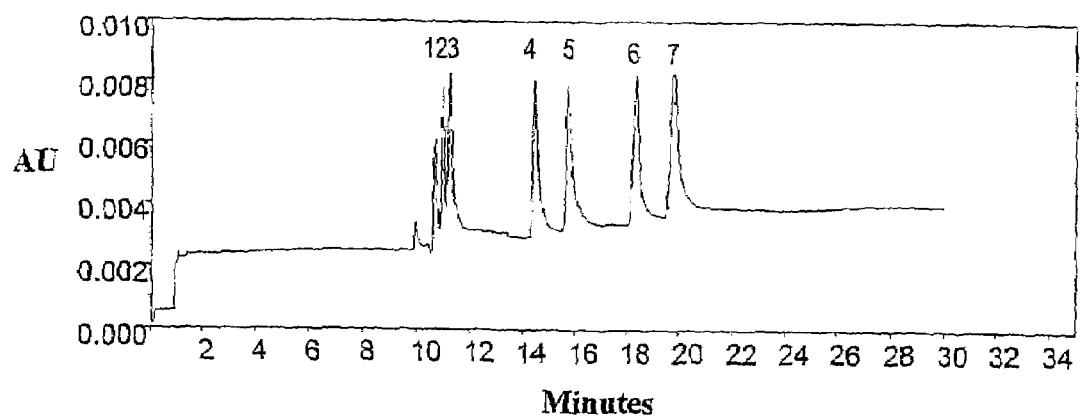
FIGS. 4(a) through (c) depict electropherograms from a single PEM-coated capillary in accordance with the present invention, made after different numbers of runs and after exposures to high and low pH conditions.
Figure 4B:
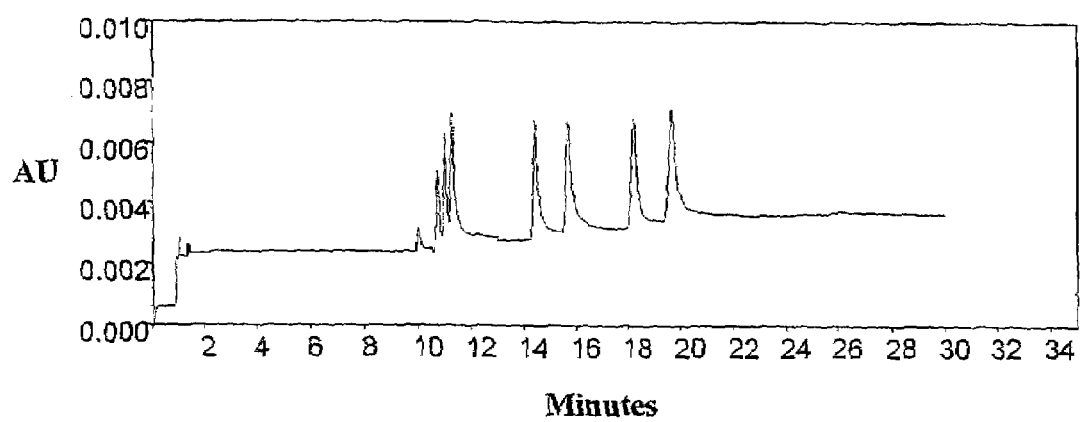
Figure 4C:
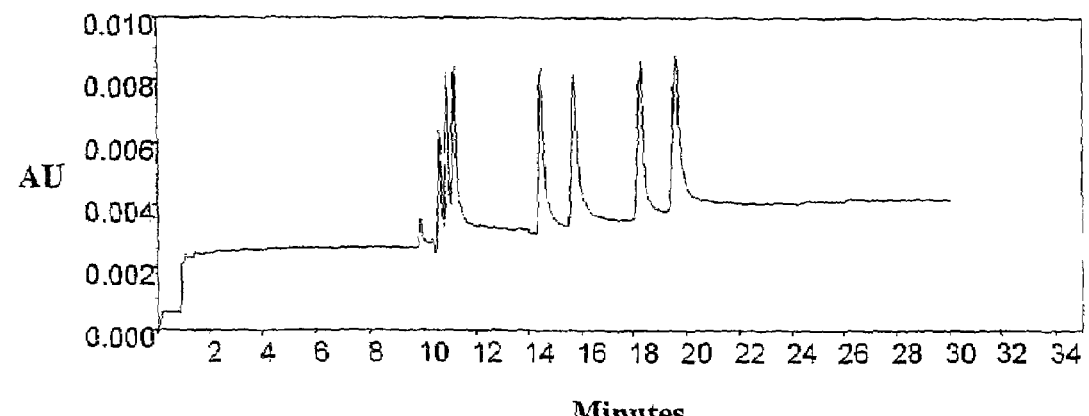

Stability of the PEM Coating. In addition to being durable, the PEM coating is also stable, even following exposure to high and low pH conditions. Phosphate buffers of pH 11.0 and 3.0 were prepared. First, 30 replicate runs were conducted with 50 mM phosphate buffer (pH 9.2) in a poly(L-SUG) PEM capillary. The applied voltage was 20 kV. The $10^{th}$ run (FIG. 4(a)) had a $\mu_{eo}$ of $2.39 \times 10^{-3}$ $cm^2V^{-1}s^{-1}$. The capillary was then flushed with 50 mM phosphate buffer (pH 11.0) for 100 minutes, and then rinsed with 50 mM phosphate buffer (pH 9.2) for 30 minutes. An electropherogram obtained after the exposure to pH 11.0 (FIG. 4(b)) (run 40) had a $\mu_{eo}$ of $2.37 \times 10^{-3}$ $cm^2V^{-1}s^{-1}$. Then the same procedure was followed with 50 mM phosphate buffer (pH 3.0). One of the runs that was performed after the pH 3.0 exposure (FIG. 4(c)) (run 110) had a $\mu_{eo}$ of $2.37 \times 10^{-3}$ $cm^2V^{-1}s^{-1}$. We thus demonstrated that the PEM coating had extraordinary stability under exposure to high and low pH conditions, over at least the range pH 3 to 11.

Figure 5A:
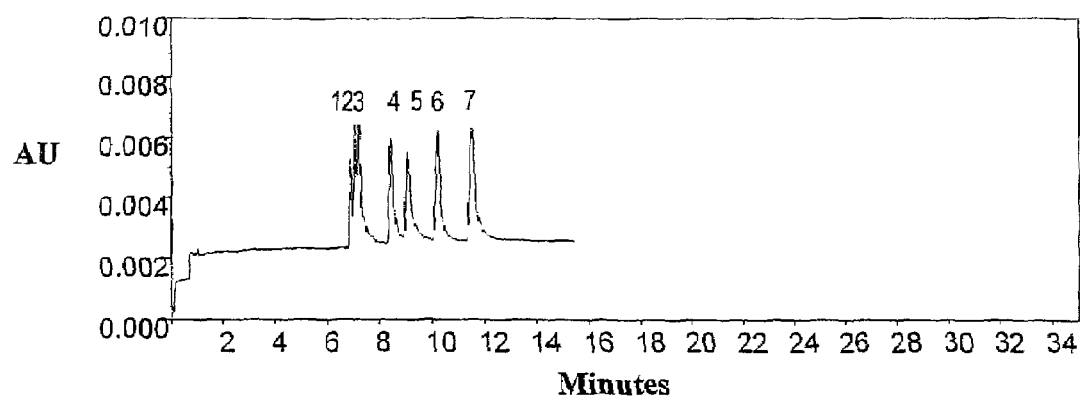
FIGS. 5(a) through (c) depict electropherograms from a single PEM-coated capillary in accordance with the present invention, made at different applied voltages.
Figure 5B:
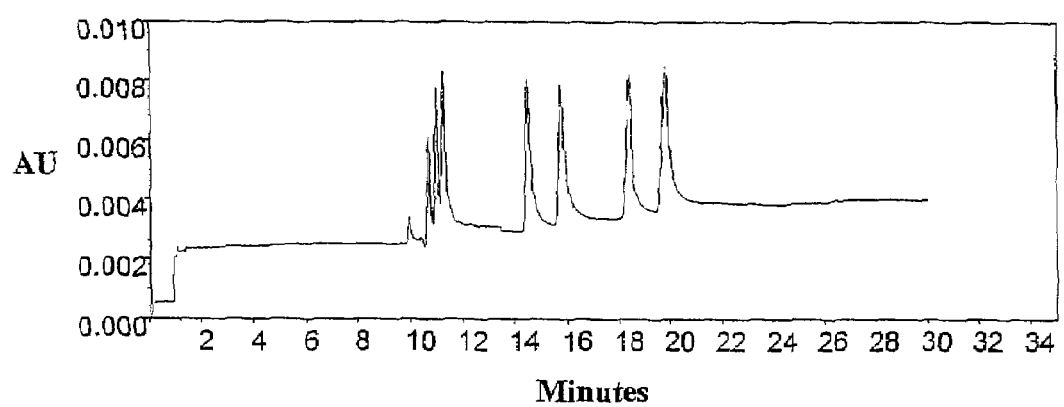
Figure 5C:
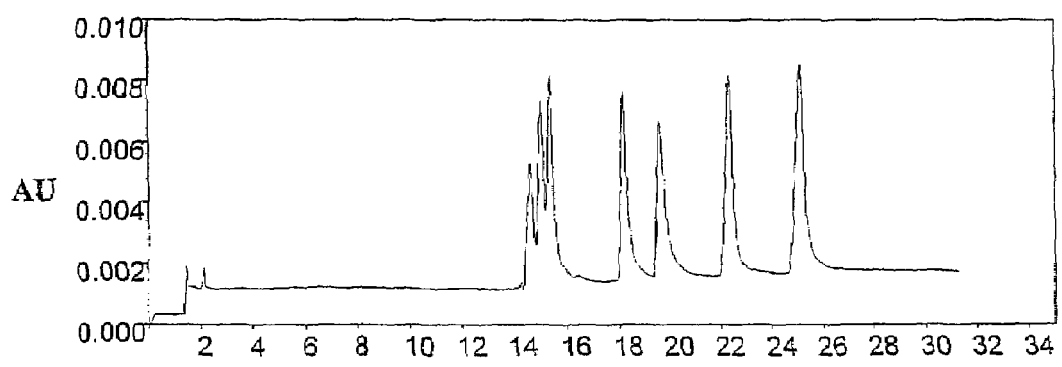

Note that in FIG. 4 (as well as in FIGS. 5-7), the labels on the peaks refer to the corresponding compound from FIG. 1.

Figure 1E:
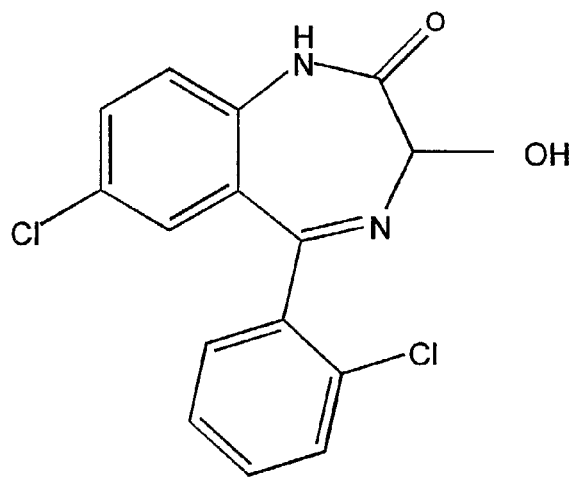
Figure 1F:
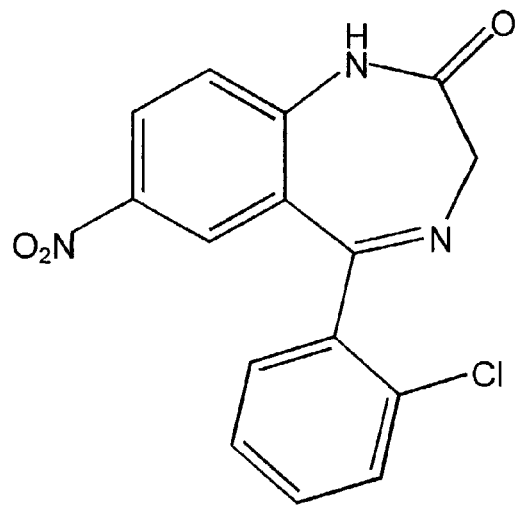
Figure 1G:
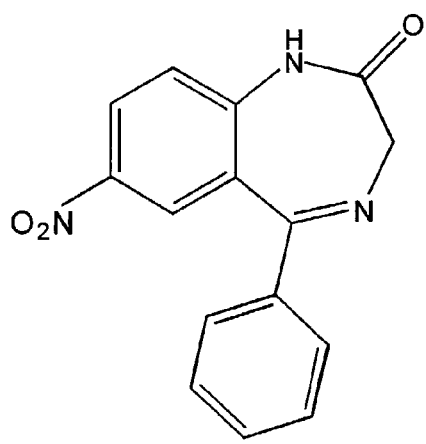
Figure 1H:
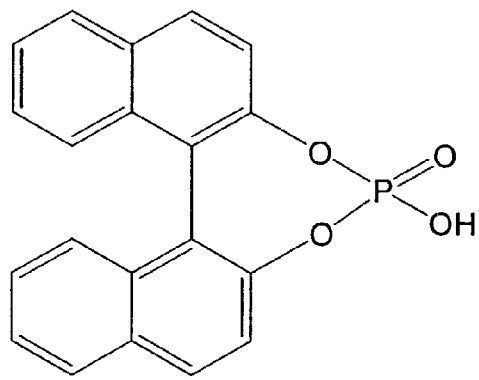
Figure 2B:
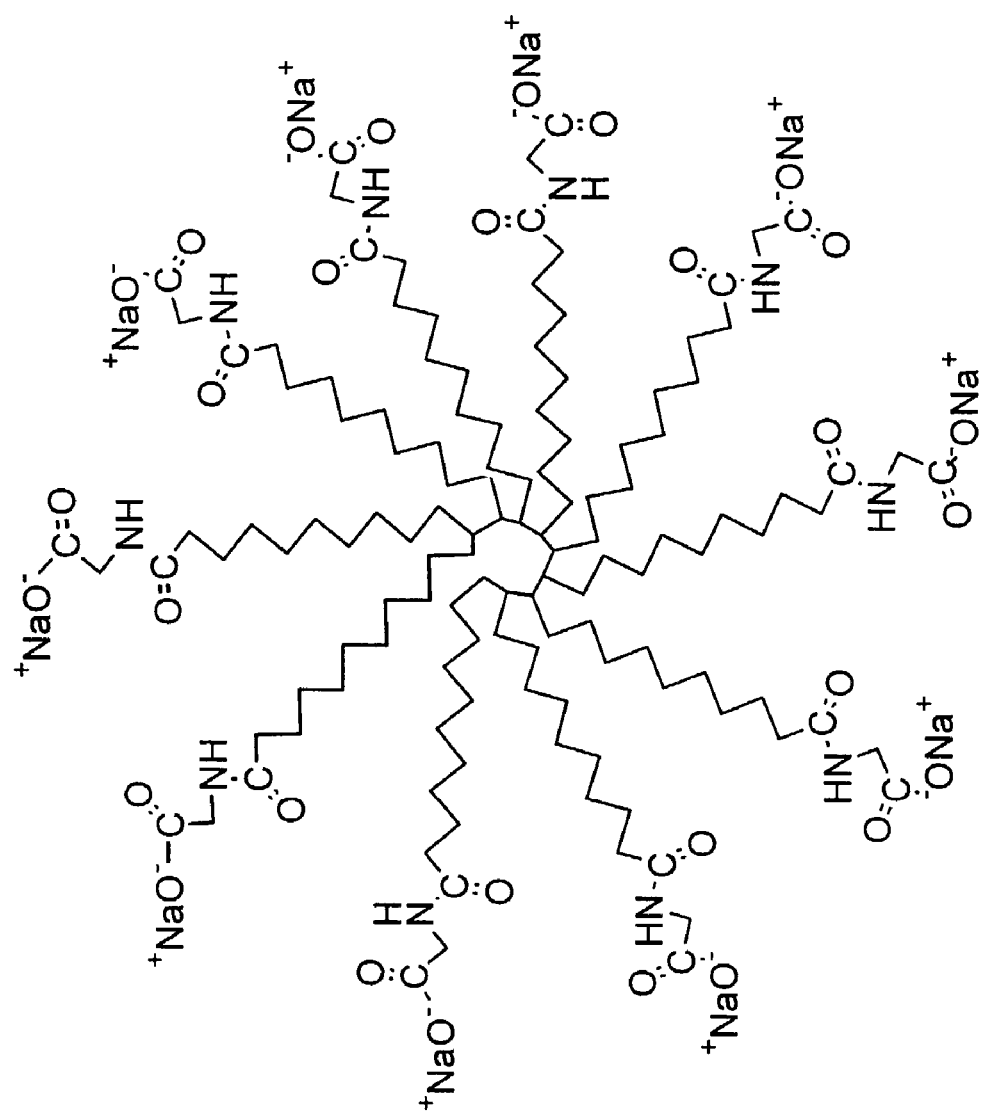
FIG. 2(b) depicts that of polymeric SUG.
Figure 2A:
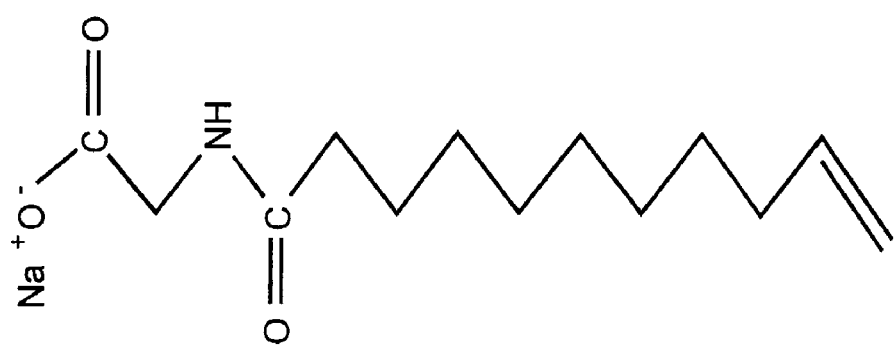
FIG. 2(a) depicts the structure of monomeric SUG.
Figure 2D:
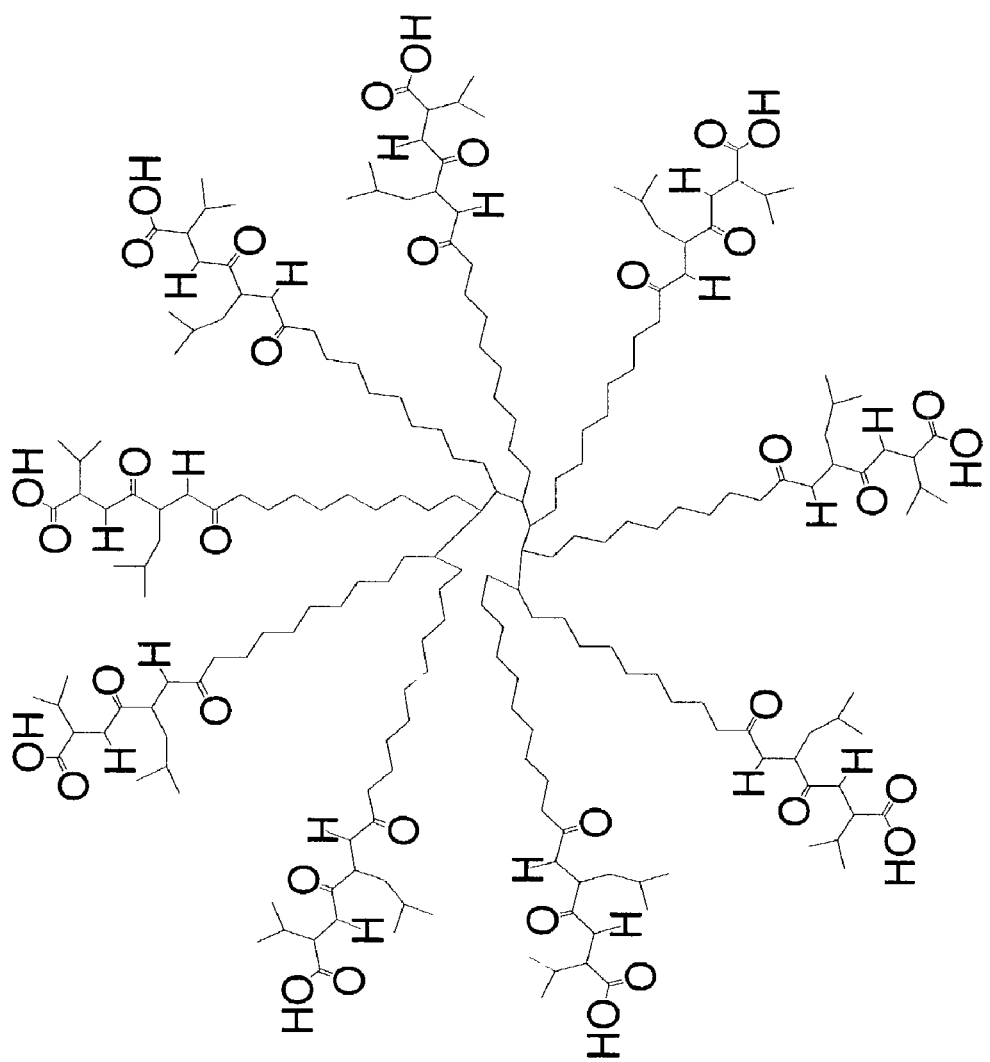
FIG. 2(d) depicts that of polymeric LV.
Figure 2C:
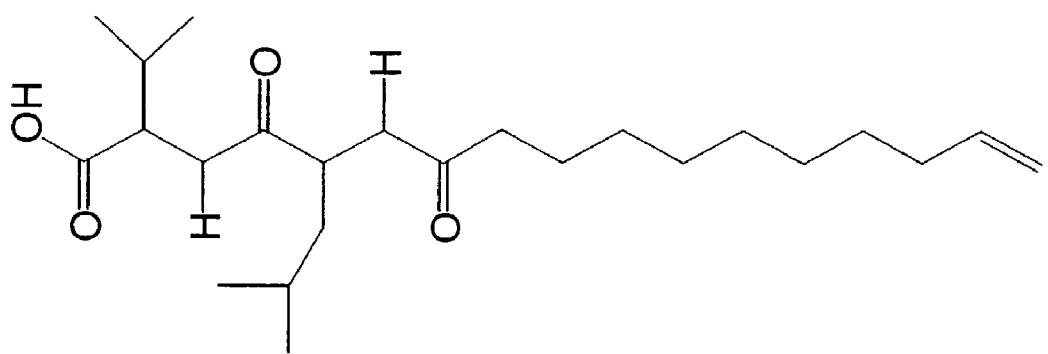
FIG. 2(c) depicts the structure of monomeric LV.

As examples, peak a corresponds to the compound shown in FIG. 1(a), namely flunitrazepam; and peak e corresponds to the compound shown in FIG. 1(e), namely lorazepam.

EXAMPLES 12 THROUGH 15

Reproducibility. The reproducibility of separations obtained with the PEM coating was evaluated by calculating the relative standard deviations (RSDs) in $\mu_{eo}$, which are reported in Table 1. The run-to-run RSD was obtained from 50 consecutive electrophoresis runs. Both the day-to-day and capillary-to-capillary RSDs were obtained from five replicate analyses. The week-to-week RSD was obtained from three replicate analyses. All RSDs were below 0.01, demonstrating very high reproducibility.

TABLE 1

|  | average $t_0$ (minutes) | RSD |
| --- | --- | --- |
| run-to-run | 9.990 | 0.0078 |
| day-to-day | 9.982 | 0.0081 |
| week-to-week | 9.930 | 0.0086 |
| capillary-to-capillary | 9.950 | 0.0093 |

EXAMPLES 16 THROUGH 18

Voltage Study. The PEM-coated capillary was used to separate seven benzodiazepines. We observed the effects of varying the applied voltage on the efficiency, resolution, and analysis time for the benzodiazepines using a mobile phase of 50 mM $Na_2HPO_4$ at 25° C. As expected, increasing the voltage decreased the retention times. At 30 kV (FIG. 5(a)), the analytes eluted faster and with higher efficiency, but at lower resolution. By contrast, at 15 kV (FIG. 5(c)) the migration times were longer, and the resolution was higher, but the efficiency was lower. There was only a small difference between analyte resolution at 15 kV (FIG. 5(c)) and at 20 kV (FIG. 5(b)).

EXAMPLES 19 THROUGH 21

Figure 6A:
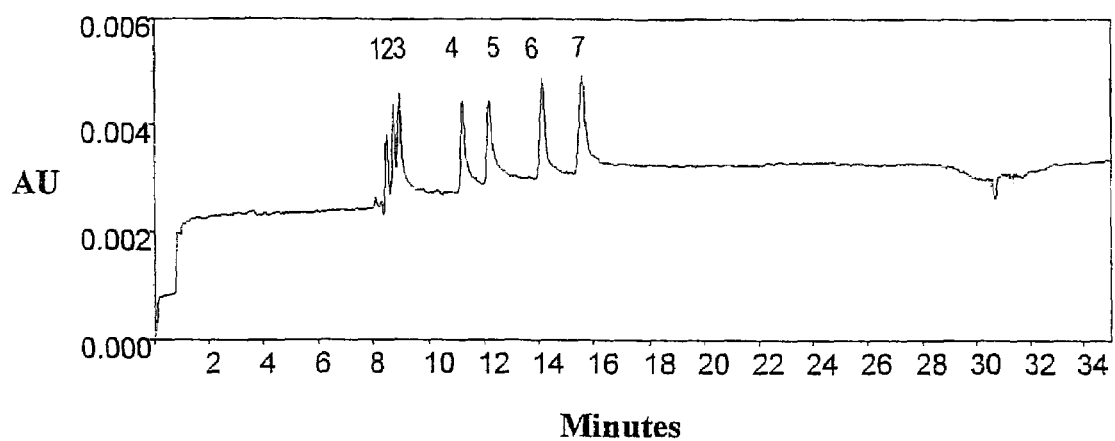
FIGS. 6(a) through (c) depict electropherograms from a single PEM-coated capillary in accordance with the present invention, made at different temperatures.
Figure 6B:
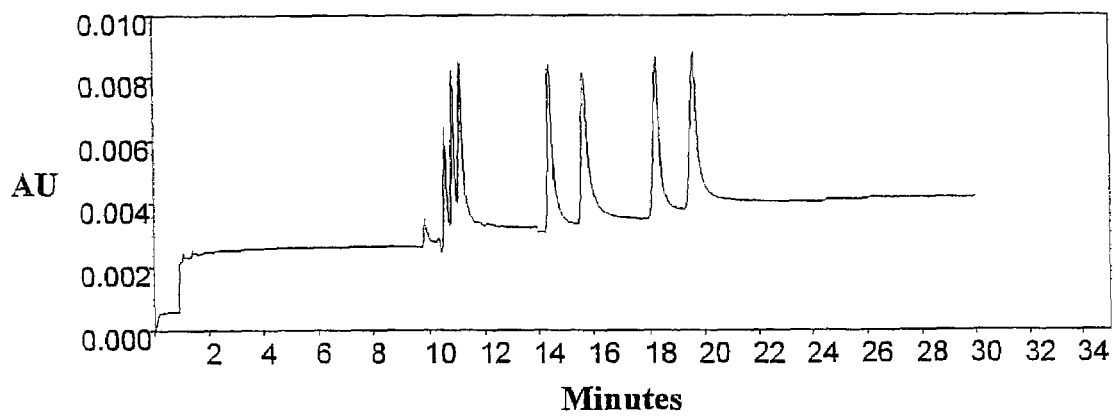
Figure 6C:
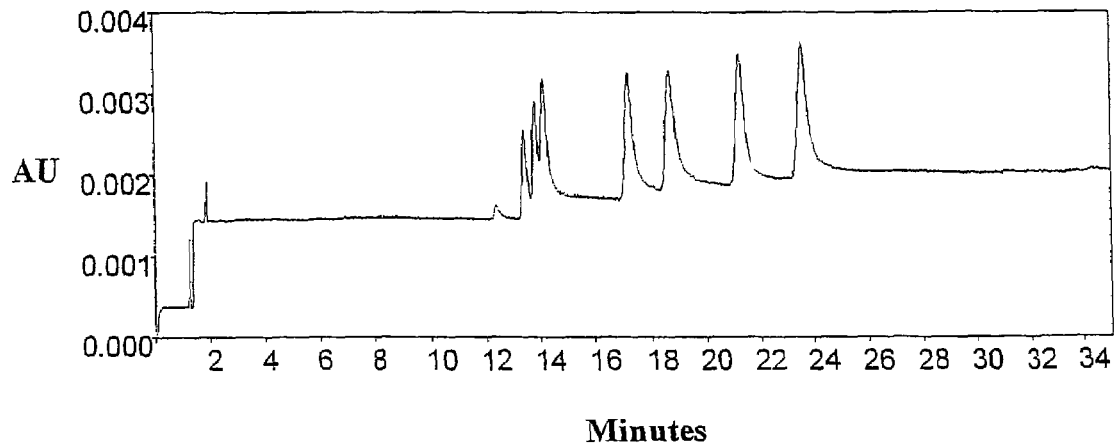

Temperature Study. We also examined the effect of temperature on the separation of the benzodiazepines, over the range 15° C. to 35° C. As shown in FIGS. 6(a) (35° C.), 6(b) (25° C.), and 6(c) (15° C.), the retention times decreased at higher temperature, as did efficiency. In addition, electroosmotic mobility increased as temperature increased, likely due to a decrease in electrolyte viscosity.

EXAMPLES 21 and 22

Figure 7A:
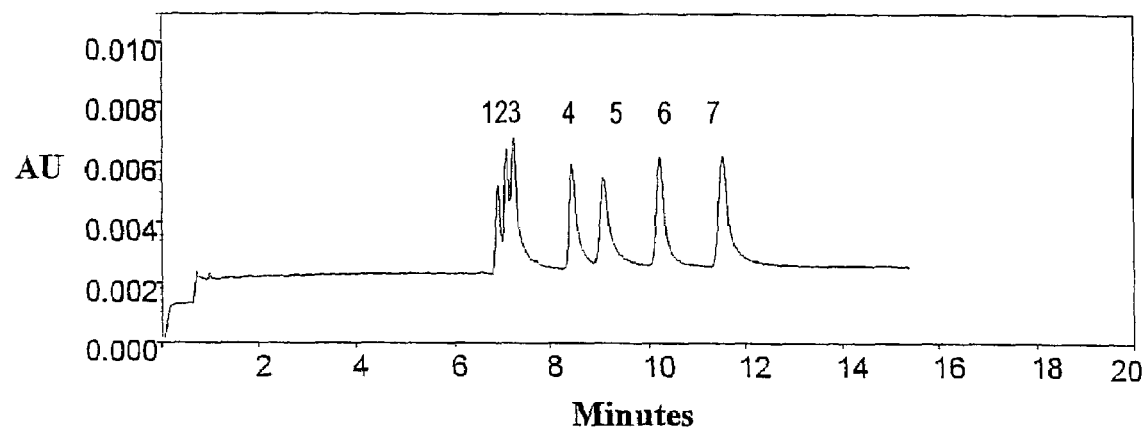
FIGS. 7(a) and (b) depict separations of benzodiazepines obtained with PEM-coated capillaries formed with polymerized micelles, and unpolymerized surfactant monomers, respectively.
Figure 7B:
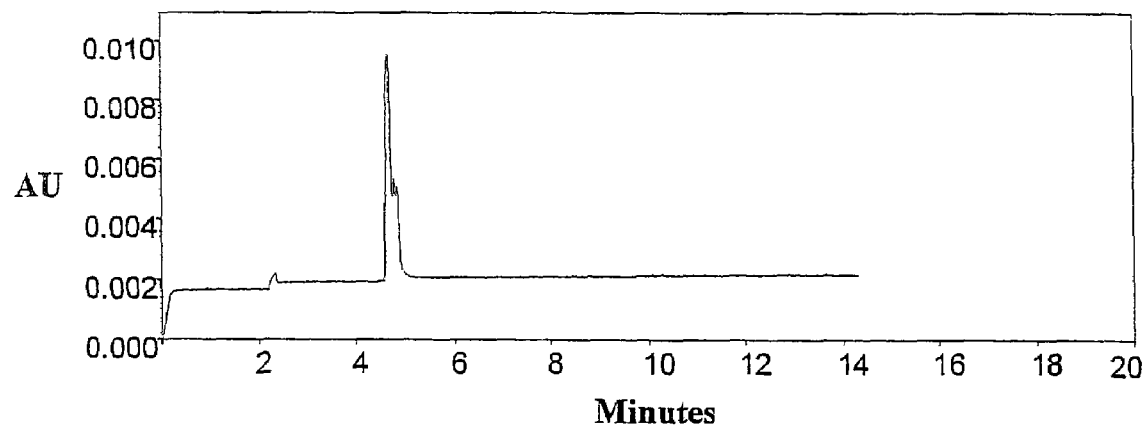

Comparison Between Monomeric and Polymeric Surfactants. We also examined whether polymerized micelles were indeed needed to form an effective, stable, and useful PEM, or whether similar results might be achieved with the corresponding monomeric surfactants. We prepared two PEM coatings for comparison: one was prepared with poly (L-SUG) as described above, and the other was prepared with monomeric(L-SUG) as otherwise described above. In each case, the anionic surfactant used in constructing the PEM coating was applied as a 0.5% (w/v) solution. The seven benzodiazepines were again used as the test solutes, in $Na_2HPO_4$ (pH 9.2) electrolyte. The applied voltage was 30 kV. The separations attained with the poly(L-SUG) PEM coating are illustrated in FIG. 7(a), and those with the monomeric(L-SUG) coating in FIG. 7(b). The contrast was striking. While seven distinct peaks were seen for the poly(L-SUG) coating, almost no separation was seem with the monomeric (L-SUG) coating, even though the concentration of the monomeric surfactant (0.5% w/v, or 19 mM) was nearly three times higher than the critical micelle concentration of the unpolymerized surfactant (7 mM). The PEM coating formed with the polymerized micelles provided substantially better discrimination of the hydrophobic analytes than did that formed with the corresponding conventional micelle. In a normal (i.e., unpolymerized) micellar system in solution, the dynamic equilibrium between surfactant monomers and micellar aggregates can adversely affect separation efficiency. An analogous dynamic equilibrium likely reduces the stability of a PEM coating made with normal (unpolymerized) micelles, thereby reducing the resolution of analyte separation. By contrast, polymeric micelles do not experience such problems, because the covalent bonds between monomers eliminate the dynamic equilibrium, resulting in a more stable PEM coating.

EXAMPLE 23

Figure 8:
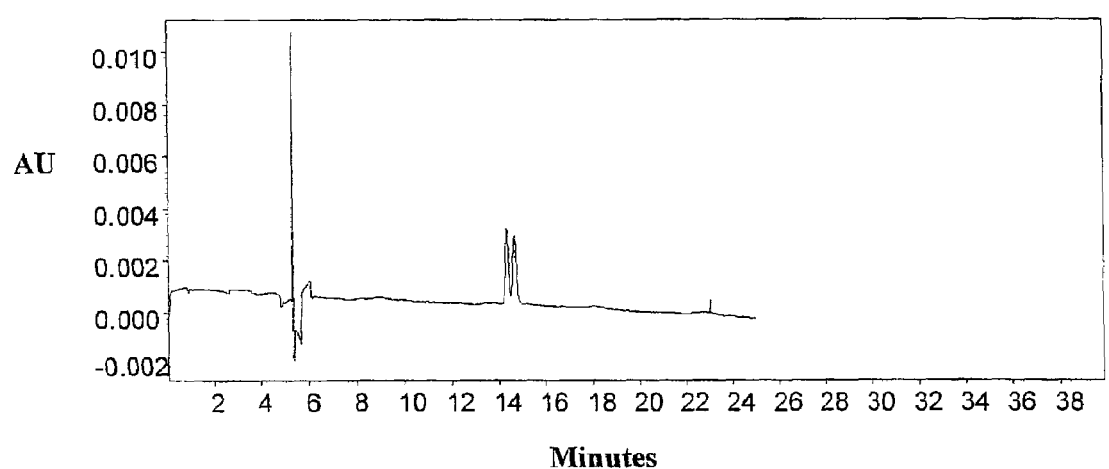
FIG. 8 depicts a chiral separation of the enantiomers of BNP.

Chiral Separation of BNP Enantiomers. FIG. 8 illustrates the chiral separation of the enantiomers of BNP using a single-bilayer of PDADMAC/poly(L-SULV). Injections were conducted at 0.3 psi for 2 seconds. The electrolyte was 100 mM Tris and 10 mM $Na_2HPO_4$ (pH 10). The applied voltage was 30 kV, the temperature 25° C., the capillary 57 cm (50 cm effective length)×50 μm i.d., and detection was at 214 nm. As shown in FIG. 8, this bilayer separated the BNP enantiomers in less than fifteen minutes with high resolution. (The strong peak around 5.5 minutes corresponds to the elution time of MeOH.)

EXAMPLE 24

Figure 9A:
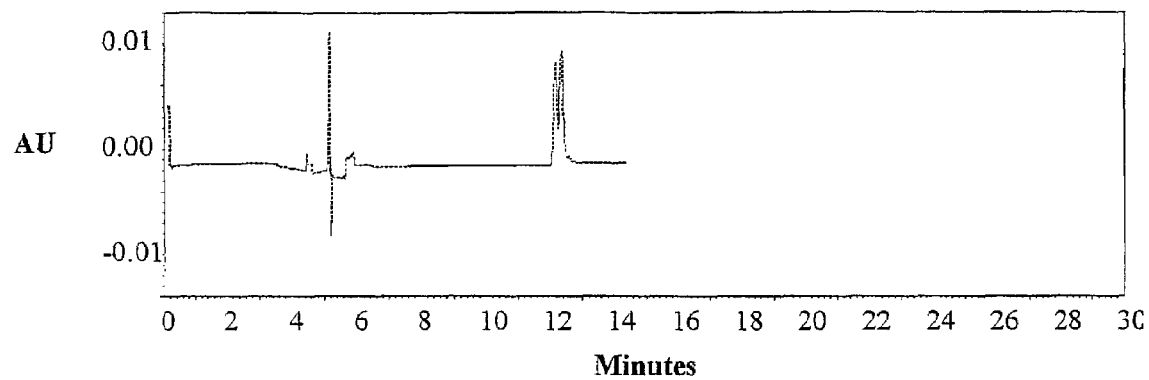
FIGS. 9(a)-(d) depict chiral separations of the enantiomers of BNP under different electrolyte conditions.
Figure 9B:
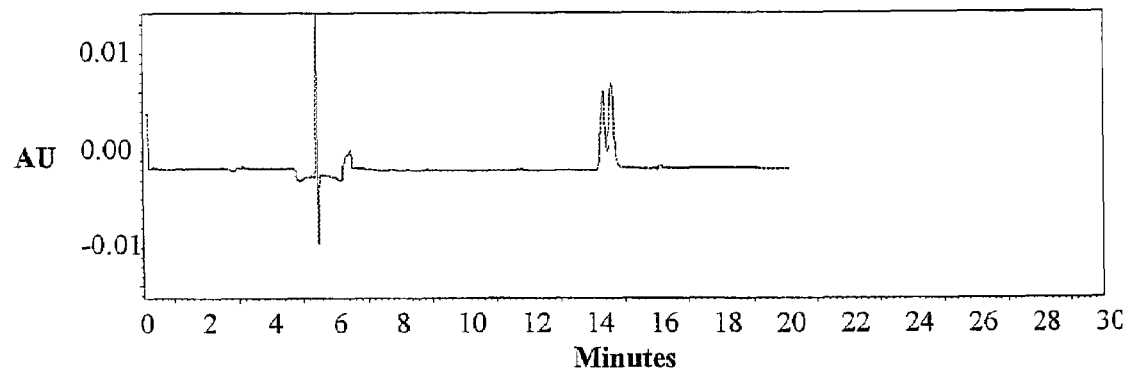
Figure 9C:
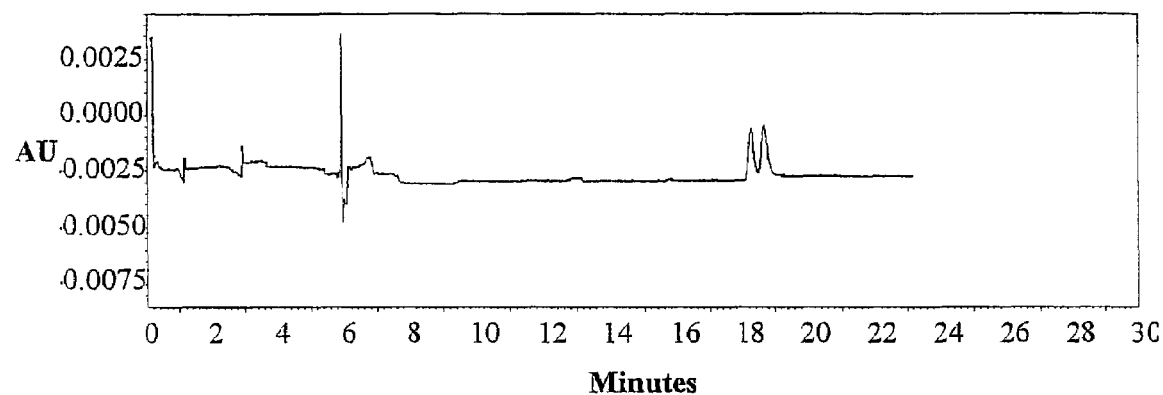
Figure 9D:
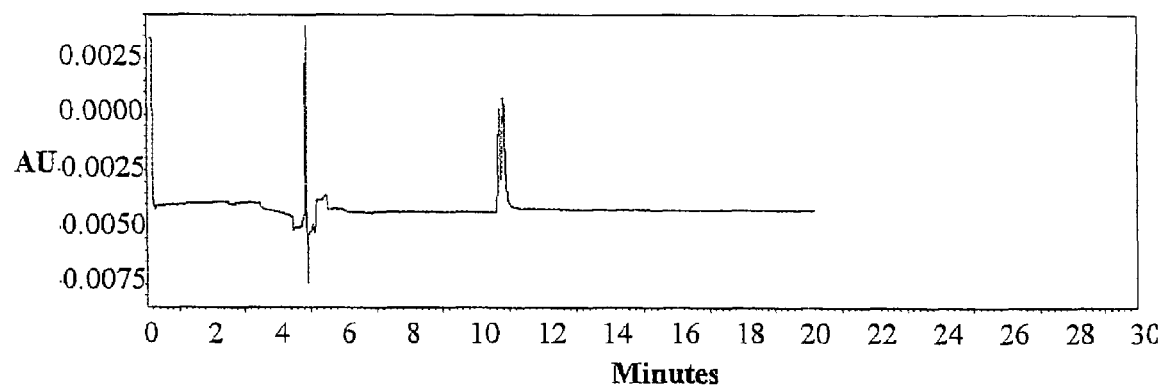
Figure 10:
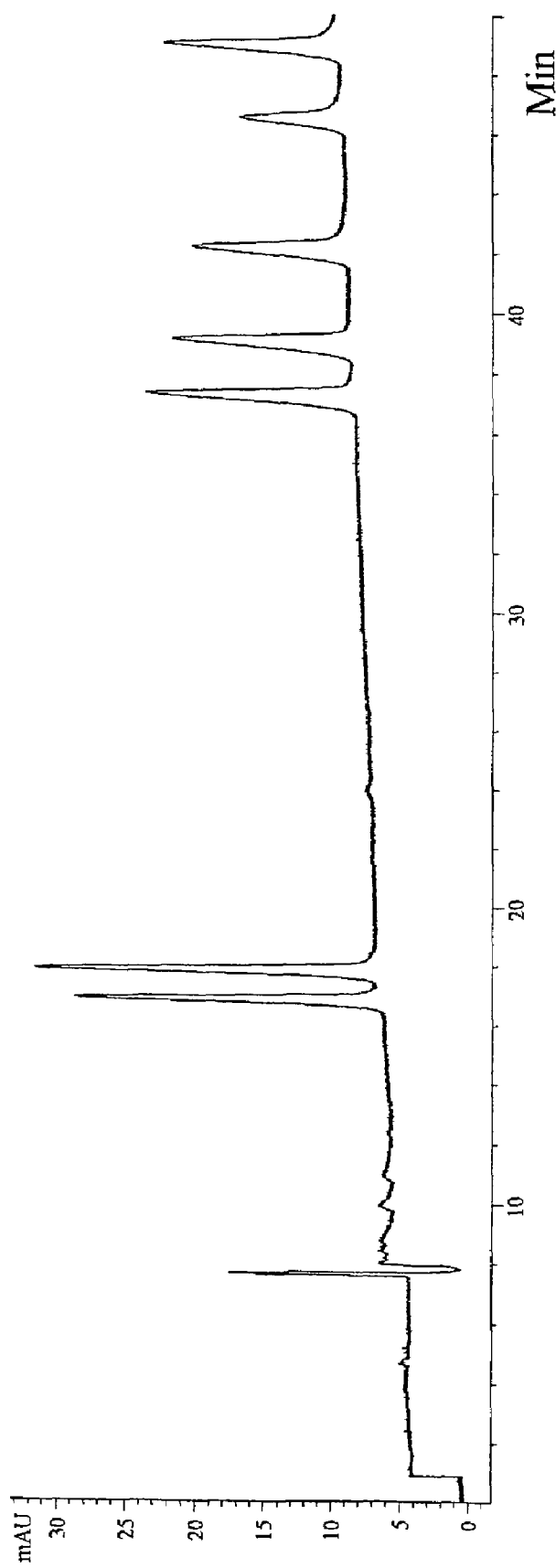
FIG. 10 depicts the separation of phenol and several substituted phenols from one another with a single coating of the zwitterionic polymer PDMAPS.

Chiral Separation of BNP Enantiomers. FIGS. 9(a)-(d) illustrate additional chiral separations of the enantiomers of BNP using a single-bilayer of PDADMAC/poly(L-SULV). Injections were conducted at 0.5 psi for 3 seconds. The electrolyte was 100 mM Tris and 10 mM $Na_2HB_4O_7$ (pH 10). The applied voltage was 30 kV, the temperature 25° C., the capillary 57 cm (50 cm effective length)×50 μm i.d., and detection was at 214 nm. In FIG. 9(a), no additional electrolytes were added. In FIG. 9(b), 10 mM NaCl was present. In FIG. 9(c), 50 mM NaCl was present. In FIG. 9(d), 5 mM of ionic 1-ethyl-3-methyl-1H-imidazolium hexafluorophosphates were added. As shown, the bilayer separated the BNP enantiomers in twelve to nineteen minutes with high resolution, with the best separation corresponding to the 50 mM NaCl. (The strong peak around 5-6 minutes in each figure corresponds to the elution time of MeOH.)

EXAMPLE 25

Coating particles. In an alternative embodiment, multilayers are coated onto particles that are used to pack a separation column. For example, a column is packed with liquid chromatography-grade particles that are coated by a method generally similar to that previously described for coating the open-tubular columns. In one embodiment, 3.28 μm silica-based beads are coated by alternating rinses with solutions of positively-charged polymers (e.g., PDADMAC) and negatively-charged polymeric micelles (e.g., poly(L-SUG). Approximately 0.5 gram quantities of silica are coated at a time. A quantity of silica is placed in a centrifuge tube. To the tube is added 10 mL of 0.1 M sodium hydroxide. The tube is placed on a mechanical shaker for 30 minutes, and is then centrifuged to promote separation of the two phases. The solution is decanted, leaving the deprotonated silica. A 10 mL aliquot of water is then added to the tube, the tube is shaken for 5 minutes, and is then decanted. This water rinse is repeated twice to remove excess base. Then a 10 mL aliquot of cationic PDADMAC solution (0.5% in 0.2 M NaCl is added to the tube, and the tube is shaken for 30 minutes, decanted, and rinsed with water twice. Next the anionic polymeric micelle poly(L-SUG) (0.5% in 0.2 M NaCl) is added to the tube, and the tube is shaken for 30 minutes, decanted, and rinsed with water twice. Optionally, the sequence of rinsing with PDADMAC and poly(L-SUG) may be repeated to build up multiple bilayers. After the layers are formed on the surface of the silica particles, the silica is allowed to dry and is then used to pack separation columns.

EXAMPLES 26-28

Zwitterionic bilayer. In an alternative embodiment, a bilayer in accordance with the present invention is made with a zwitterionic polymer in place of separate cationic and anionic polymers. When a zwitterionic polymer is used, the bilayer may be prepared with only a single rinse of the capillary; although it is also possible to use multiple rinses of the zwitterionic polymer if desired. For example, we have used the zwitterionic poly (3-dimethyl methacryloyloxy-ethyl ammonium propane sulfonate) (PDMAPS) in a PEM coating.

The zwitterionic monomer 3-dimethyl methacryloyloxy-ethyl ammonium propane sulfonate (DMAPS) was purchased from Aldrich Chemical Co. (Milwaukee, Wis.). The analytes used in one separation comprised phenol and various substituted phenol compounds: 3,5-dimethyl phenol; 4-methyl phenol; phenol; 4-fluorophenol; 4-chlorophenol; 3-chlorophenol; and 3-bromophenol. The analytes used in a second separation comprised several peptides: bradykinin, bradykinin fragment 1-5, substance P, [Arg]-vasopressin, luteinizing hormone releasing hormone, bombesin, leucine enkephalin, methionine enkephalin, and oxytocin. Analytes were purchased from Sigma Chemical Company (St. Louis, Mo.). Sodium phosphate buffer was purchased from Fischer Scientific (Fair Lawn, N.J.).

The polymer PDMAPS was synthesized by free radical-polymerization of the monomer DMAPS. Potassium peroxosulfate (0.1%) was added to 5 g of the monomer, dissolved in 20 mL deionized water in a reaction flask. Reaction was carried out over a water-bath at 60° C. for 15 hours. The resulting polymer was washed in acetone several times to remove unreacted monomer. The molecular weight, as measured by gel permeation chromatography, was about 49 kDa.

The interior wall of a capillary was coated with PDMAPS. A 0.5 cm detection window was formed by burning off the external polyimide coating of the capillary. The capillary was first rinsed with water for five minutes, followed by conditioning with 1 M NaOH for thirty minutes. The capillary was then rinsed with water for fifteen minutes, and with then with a 3.8% solution of PDMAPS in 0.1 M NaCl for thirty minutes. Then, following a fifteen-minute waiting period, water was flushed through the capillary for five minutes to rinse out any excess polymer. Before analyte injections the capillary was conditioned with the running buffer for fifteen minutes.

FIG. 10 illustrates the separation of phenol and the several substituted phenols from one another with a single coating of PDMAPS. Injections were conducted at 30 mbar for 1 second. The electrolyte was 20 mM $Na_2HPO_4$ (pH 2.5). The applied voltage was 15 kV, the temperature 20° C., the capillary 57 cm (50 cm effective length)×50 µm i.d., and detection was at 200 nm. As shown in FIG. 10, the zwitterionic bilayer separated the phenol and substituted phenols from one another over a span of about fifty minutes with high resolution. From left to right, the eluted analytes were as follows: 3,5-dimethyl phenol; 4-methyl phenol; phenol; 4-fluorophenol; 4-chlorophenol; 3-chlorophenol; and 3-bromophenol. The first peak shown, around 8 minutes, was methanol.

Figure 11:
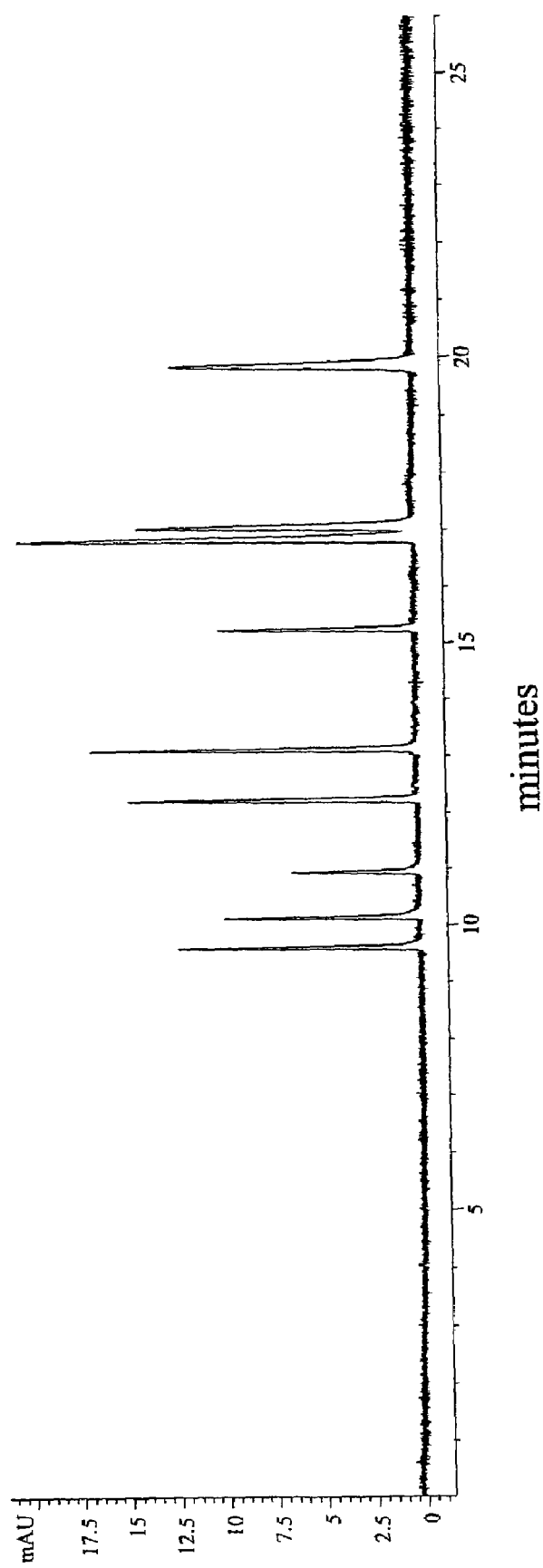
FIG. 11 depicts the separation of nine peptides from one another with a single coating of the zwitterionic polymer PDMAPS.

FIG. 11 illustrates the separation of the nine peptides from one another with a single coating of PDMAPS. Injections were conducted at 30 mbar for 3 seconds. The electrolyte was 20 mM $Na_2HPO_4$ (pH 2.5). The applied voltage was 20 kV, the temperature 20° C., the capillary 58 cm (50 cm effective length)×50 µm i.d., and detection was at 200 nm. As shown in FIG. 10, the zwitterionic bilayer separated the nine peptides from one another over a span of about twenty minutes with high resolution. From left to right, the eluted analytes were as follows: bradykinin, bradykinin fragment 1-5, substance P, [Arg]-vasopressin, luteinizing hormone releasing hormone, bombesin, leucine enkephalin, methionine enkephalin, and oxytocin.

Zwitterionic polymers that may be used in this embodiment of the invention include, for example, poly (3-dimethyl methacryloyloxyethyl ammonium propane sulfonate) (PDMAPS); coco (amidopropyl) hydroxydimethylsulfobetaine (Rewoteric AM CAS U); dodecyidimethyl (3-sulfopropyl) ammonium hydroxide; and hexadecyldimethyl (3-sulfopropyl) ammonium hydroxide Miscellaneous While most of the examples given above are examples of bilayers, more generally, the polyelectrolytes may be deposited in layers. Such layers may be, but are not necessarily, bilayers. It is possible, for example, to mix positively and negatively charged polymers in a single layer. Also, as previously discussed, it is possible to use zwitterionic polymers in lieu of, or in addition to, separate positively and negatively charged polymers. Most surfaces used in microchannels are negatively charged initially, such as native silica, although some are positively charged. For example, a positive charge may be imparted to silica by treating it with an aminosiloxane. Likewise, the final layer in the multilayer may be either positively or negatively charged, and the polymerized micelles may be either positively or negatively charged.

While it is customary to speak of "layers" as discrete entities, those skilled in the art will appreciate that individual polymer layers may interpenetrate one another; a clearly demarcated stratification may or may not exist in the finished multilayer. A "layer" may therefore be considered to be a thickness increment to a growing or incipient multilayer following exposure to one or more of the charged components being used to build the multilayer.

As used in the specification and claims, unless context clearly indicates otherwise, a "microchannel" should be understood to mean an enclosed channel having an aspect ratio of about 10 or greater, and having an average cross-section diameter between about 1 µm and about 500 µm. A diameter between about 50 µm and about 75 µm is usually preferred. The substrate in which the microchannel is formed may be any substrate such as is used in the arts of chromatography and microfluidics, including, for example, silica, fused silica, and polymers such as poly (methyl methacrylate) (PMMA).

The complete disclosures of all references cited in this specification are hereby incorporated by reference. Also incorporated by reference is the complete text of the following paper, which is not prior art to the present application: C. Kapnissi et al., *Analytical Chem.*, vol. 74, pp. 2328 ff(2002). In the event of an otherwise irreconcilable conflict, however, the present specification shall control.

We claim:

1. A separation apparatus, wherein said apparatus is suitable for reuse for many separations, said apparatus comprising:
   (a) a substrate containing a microchannel; and
   (b) a multilayer coating bound to the interior of the microchannel; wherein:
      (i) said multilayer coating comprises a layered mixture of positively charged polymer molecules and negatively charged polymer molecules; and
      (ii) at least some of said charged polymer molecules in the innermost negatively charged polymer layer comprise charged polymerized micelles.

2. Apparatus as recited in claim 1, wherein said substrate comprises a fused silica capillary having an internal diameter between about 5 μm and about 200 μm.

3. Apparatus as recited in claim 1, wherein:
   (a) said multilayer coating comprises n layers, wherein n is an integer greater than or equal to 2;
   (b) said layers alternate between a layer comprising positively charged polymer molecules, and a layer comprising negatively charged polymer molecules, wherein said positively charged and negatively charged layers bind to one another electrostatically;
   (c) the charge of polymer molecules of the first said layer is opposite to the surface charge on the interior of said microchannel; and
   (d) the n-th layer comprises charged polymerized micelles.

4. Apparatus as recited in claim 1, wherein at least some of said polymerized micelles are chiral.

5. Apparatus as recited in claim 4, wherein at least one polymeric layer within said multilayer coating was deposited on the interior of the microchannel from a solution comprising an ionic liquid, wherein the solution was substantially free of sodium chloride.

6. Apparatus as recited in claim 1, wherein at least some of said positively charged polymer molecules are selected from the group consisting of polymers containing a quaternary ammonium group, poly (diallyldimethylammonium chloride), poly (vinylbenzyltrimethyl ammonium chloride), ionenes, cationic polyacrylamides, poly (acryloxyethyltrimethyl ammonium chloride), poly (methacryloxy(2-hydroxy) propyltrimethyl ammonium chloride), polymers containing a pyridinium group, poly (N-methylvinylpyridine), poly (N-alkylvinylpyridines), protonated polyamines, poly (allylaminehydrochloride), polyethylenimine polybrene, corresponding salts, and corresponding copolymers.

7. Apparatus as recited in claim 1, wherein said positively charged polymer molecules comprise poly (diallyldimethylammonium chloride).

8. Apparatus as recited in claim 1, wherein at least some of said negatively charged polymer molecules are selected from the group consisting of polyelectrolytes containing a sulfonate group, poly (styrenesulfonic acid), poly (2-acrylamido-2-methyl-1-propane sulfonic acid), sulfonated poly (ether ether ketone), sulfonated lignin, poly (ethylenesulfonic acid), poly (methacryloxyethylsulfonic acid), polycarboxylates, poly (acrylic acid), poly (methacrylic acid), carrageenan, dextran sulfate, corresponding salts, and corresponding copolymers.

9. Apparatus as recited in claim 1, wherein at least some of said micelles are selected from the group consisting of poly (sodium N-undecylenic sulfate), poly (sodium N-undecylenyl-L-glycinate), poly (sodium N-undecylenyl-L-leucine-L-valinate), poly (sodium N-undecylenyl-L-valinate), poly (sodium N-undecylenyl-L-leucine-L-alininate), and poly (sodium N-undecylenyl-L-glycine-L-leucinate).

* * * * *